US006537526B2

(12) United States Patent
Libin

(10) Patent No.: US 6,537,526 B2
(45) Date of Patent: Mar. 25, 2003

(54) ANTIMICROBIAL SOLUTIONS

(75) Inventor: Barry M. Libin, Great Neck, NY (US)

(73) Assignee: BML Pharmaceuticals, Inc., Manhasset, NY (US)

( * ) Notice: Subject to any disclaimer, the term of this patent is extended or adjusted under 35 U.S.C. 154(b) by 0 days.

(21) Appl. No.: 09/851,365

(22) Filed: May 8, 2001

(65) Prior Publication Data

US 2002/0187107 A1 Dec. 12, 2002

(51) Int. Cl.[7] .............................. A61K 7/16; A61K 7/22
(52) U.S. Cl. ........................................... 424/54; 424/49
(58) Field of Search ..................... 424/49–58

(56) References Cited

U.S. PATENT DOCUMENTS

| 5,100,650 | A | * | 3/1992 | Carlin | 424/54 |
|---|---|---|---|---|---|
| 5,236,699 | A | * | 8/1993 | Libin | 424/54 |
| 5,256,396 | A | * | 10/1993 | Piechota | 424/49 |
| 5,407,664 | A | * | 4/1995 | Konopa | 424/54 |
| 5,500,448 | A | * | 3/1996 | Cummins et al. | 514/717 |
| 5,560,906 | A | * | 10/1996 | Scodari et al. | 424/54 |
| 5,686,063 | A | * | 11/1997 | McLaughlin et al. | 424/54 |
| 5,723,106 | A | * | 3/1998 | Buch et al. | 424/49 |
| 5,945,087 | A | * | 8/1999 | Nelson et al. | 424/49 |
| 5,945,088 | A | * | 8/1999 | Delli Santi et al. | 424/49 |
| 6,235,267 | B1 | * | 5/2001 | Delli Santi et al. | 424/49 |
| 6,245,321 | B1 | * | 6/2001 | Nelson et al. | 424/49 |
| 6,261,540 | B1 | * | 7/2001 | Nelson | 424/53 |

* cited by examiner

*Primary Examiner*—Shep K. Rose
(74) *Attorney, Agent, or Firm*—Hedman & Costigan, P.C.

(57) ABSTRACT

A water based composition having triclosan in an amount of 0.01 to 3% by weight in combination with from 5–35% by weight of a non-toxic polyhydric alcohol and from 0.5–5% by weight of a poloxamer.

9 Claims, No Drawings

ANTIMICROBIAL SOLUTIONS

BACKGROUND OF THE INVENTION

Many compounds have been described for use on the skin and mucous membranes for various purposes. In U.S. Pat. No. 5,236,699, a formulation of triclosan and a cationic compound is described as being useful as an antiplaque mouth rinse and for other purposes. Generally, for treating solutions to be acceptable, they must be clear solutions that are stable. If these solutions form a precipitate upon standing at ambient conditions, it will not be acceptable to patients. The formulations of U.S. Pat. No. 5,236,699 are made using a solubilizer and alcohol to provide a stable clear solution of triclosan and a cationic antimicrobial compound. The concentration of triclosan in U.S. Pat. No. 5,236,699 is described at col. 3, lines 50–51 as being about 0.01 to 0.05% by weight. Due to the limited solubility of triclosan in water, a combination of ethyl alcohol and a solubilizer is used to achieve a stable and clear solution.

The presence of as little as 3–10% by weight of ethyl alcohol can cause tissue irritation, a burning sensation or drying of the skin or the mucosa. The presence of ethyl alcohol in formulations is unacceptable for various patient groups including those with alcohol dependencies, liver dysfunction, and other metabolic disorders.

It has been found that when propylene glycol is used to dissolve the flavor components, this will contribute to the tendency of the solution to become cloudy.

The use of solubilizers such as polysorbate 80 has been shown to inactivate triclosan and higher amounts of ethyl alcohol will increase the potential for problems with irritation and burning.

SUMMARY OF THE INVENTION

The applicant has found that use of a non-toxic polyhydric alcohol in combination with a polyoxy-alkylene and water will provide a stable triclosan solution where the concentration of triclosan may be up to 3% by weight.

Accordingly it is a primary object of this invention to provide a stable solution of triclosan.

It is also an object of this invention to provide a solution of triclosan without the use of ethyl alcohol.

It is also an object of this invention to provide a stable solution of triclosan having a triclosan content of up to 3% by weight.

These and other objects of the invention will become apparent from a review of the appended disclosure.

DETAILED DESCRIPTION OF THE INVENTION

The stable triclosan solutions of the invention may be used for the treatment of traumatic oral wounds, aphthous ulcers, gingival and periodontal diseases, herpes simplex lesions, acne, oral infections, e.g., the HIV virus or mucositis which is induced as a result of chemotherapy or radiation therapy for neoplastic diseases; all mucosal surfaces including genital, oral, pharyngeal, esophogeal, and other gastrointestinal linings.

The formulations may be administered directly to the surface of affected areas using soft applicators such as cotton or cloth wipes. They may be admisistered by non-pressurized spraying apparatus or by pressurized aerosol apparatus in sufficient amount to wet the affected areas.

When used for treating esophogeal or gastrointestinal areas, a dose of 5–30 ml of the solution may be orally administerd by gargling and or swallowing the solution one to six times daily. For the treatment of lower areas of the gastrointestinal tract, the solution may be directly infused using rectal tubes to place 5–30 ml of the solution of the invention in contact with the affected areas.

The formulations comprise the following ingredients (by weight):

| | | | |
|---|---|---|---|
| triclosan | 0.01–3.% | or | 0.1–1.0% |
| polyoxamers | 0.5–5% | or | 1–3% |
| polyhydric alcohol | 5–35% | or | 8–25% |
| water qs | 100% | | |

The compositions may also contain flavoring agents, coloring agents and the like.

The polyoxamers act as solubilizers for the triclosan. These materials are block copolymers of poly(oxyethylene) and poly(oxypropylene) having a molecular weight (wt. av.) of from 1000 to more than 16,000 and preferably from 12,000 to 13,000. These materials are of the formula $HO(CH_2CH_2O)_a(CH-(CH_3)(CH_2OH)_b(CH_2CH_2O)_cH$ where b is at least 15 and $(CH_2CH_2O)_a+c$ is varied from 20 to 90% by weight. The poloxamer which is available commercially as Pluronic F127 is the preferred poloxamer.

The useful polyhydric alcohols include those non-toxic polyhydroxy compounds which include glycerin, sorbitol, and polyethylene glycols having a molecular weight (wt. av.) of 200 or less.

Triclosan is 2,4,4'-trichloro-2'-hydroxydiphenyl ether which is commercially available.

A cationic antimicrobial agent may be used in the composition. These materials include chlorhexidine and quaternary ammonium salts such as cetylpyridinium chloride (CPC) which is the monohydrate of the quaternary ammonium salt of pyridine and cetyl chloride. CPC is cationic and highly soluble in water. Other cationic antimicrobial agents include benzalkonium chloride, benzethonium chloride, methylbenzethonium chloride and domiphen bromide. Chlorhexidine may be applied as the free base, or as the dihydrochloride or the gluconate salt.

The combination of triclosan and the cationic agent has the effect that the combined agents are readily adsorbed and retained on the oral mucosa while resisting removal by saliva in the oral cavity. Generally from about 0.001 to 0.3 wt % and preferably about 0.025 wt % of a cationic antibacterial agent may be employed.

A liquid formulation may be prepared with purified water, triclosan, polyhydric alcohol and a solubilizer. The solubilizer may comprise a poloxamer.

When the solution is intended for oral use, it may include an anti-caries agent which is soluble in water such as sodium fluoride, stannous fluoride or sodium monofluorophosphate in an amount which is effective to inhibit tooth decay. Generally, this amount will be from 0.01 to 4% by weight, based on the weight of the fluoride ion. The amount may be varied depending on the particular source of the fluoride ion which is chosen. Certified color may be added in a minor amount e.g. 0.1% by weight.

A typical liquid formulation will comprise:

|                        | % weight |
|------------------------|----------|
| Triclosan              | 0.200    |
| Sorbitol               | 12.000   |
| Glycerin               | 10.000   |
| Sodium Saccharin, U.S.P| 0.100    |
| Pluronic FI27, NF      | 1.000    |
| Peppermint 1FL2745     | 0.152    |
| Caramel Color AP100    | 0.0085   |
| Purified water         | qs 100.0 |

A typical fluoridated liquid formulation will comprise:

|                        | % weight  |
|------------------------|-----------|
| Triclosan              | 0.100     |
| Sodium Fluoride        | 0.020     |
| Sorbitol               | 12.000    |
| Glycerin               | 10.000    |
| Sodium Saccharin, U.S.P| 0.100     |
| Pluronic FI27, NF      | 1.000     |
| Peppermint 1FL2745     | 0.152     |
| Caramel Color AP100    | 0.0085    |
| Purified water         | qs 100.00 |

A typical liquid formulation containing a cationic agent will comprise:

|                        | % weight  |
|------------------------|-----------|
| Triclosan              | 0.100     |
| Cetyl pyridinium chloride | 0.024  |
| Sorbitol               | 12.000    |
| Glycerin               | 10.000    |
| Sodium Saccharin, U.S.P| 0.100     |
| Pluronic FI27, NF      | 1.000     |
| Peppermint 1FL2745     | 0.152     |
| Caramel Color AP100    | 0.0085    |
| Purified water         | qs 100.00 |

All percentages are by weight based on the total weight of the water based composition.

The foregoing description of a preferred embodiment of the invention has been presented for purposes of illustration and description. It is not intended to be exhaustive or to limit the invention to the precise form disclosed. Obvious modifications or variations are possible in light of the above teachings. All such obvious modifications and variations are intended to be within the scope of the appended claims.

I claim:

1. A water based composition which consists essentially of triclosan in an amount of 0.01 to 3% by weight in combination with from 5–35% by weight of a non-toxic polyhydric alcohol selected from the group consisting of glycerin, sorbitol and polyethylene glycol and from 0.5–5% by weight of poloxamer.

2. A water based composition as defined in claim 1 wherein the polyhydric alcohol is glycerin.

3. A water based composition as defined in claim 1 wherein the polyhydric alcohol is sorbitol.

4. A water based composition as defined in claim 1 wherein the poloxamer has a molecular weight of 12,000 to 13,000.

5. A water based composition as defined in claim 1 wherein the triclosan comprises from 0.1–3% by weight of the composition.

6. A water based composition as defined in claim 2 wherein the glycerin comprises 8–12% by weight of the composition.

7. A water based composition as defined in claim 1 which includes a cationic agent.

8. A water based composition as defined in claim 6 wherein the cationic agent is cetyl pyridinium chloride.

9. A water based composition as defined in claim 7 wherein the cationic agent comprises 0.024–0.3% by weight of the composition.

* * * * *